US00RE36611E

United States Patent [19]

French

[11] E Patent Number: Re. 36,611

[45] Reissued Date of Patent: Mar. 14, 2000

[54] EMERGENCY TRACHEOSTOMY APPARATUS

[76] Inventor: Ronald French, 3525 Prytania St., New Orleans, La. 70115

[21] Appl. No.: 09/024,244

[22] Filed: Feb. 17, 1998

Related U.S. Patent Documents

Reissue of:

[64] Patent No.: 5,546,939
Issued: Aug. 20, 1996
Appl. No.: 08/349,322
Filed: Dec. 5, 1994

[51] Int. Cl.[7] ..... A61M 16/00

[52] U.S. Cl. ..... 128/207.29; 128/200.26

[58] Field of Search ..... 128/200.26, 207.29

[56] References Cited

U.S. PATENT DOCUMENTS

| | | | |
|---|---|---|---|
| Re. 34,086 | 10/1992 | George | 128/200.26 |
| 300,285 | 6/1884 | Russell | 128/207.29 |
| 2,873,742 | 2/1959 | Shelden | 128/207.29 |
| 2,991,787 | 7/1961 | Shelden et al. | 128/207.29 |
| 3,182,663 | 5/1965 | Abelson | 128/207.29 |
| 3,307,551 | 3/1967 | Violet, Jr. | 128/207.29 |
| 3,384,087 | 5/1968 | Brummelkamp | 128/207.29 |
| 3,556,103 | 1/1971 | Calhoun | 128/347 |
| 3,606,669 | 9/1971 | Kemble | 128/200.26 |
| 3,613,684 | 10/1971 | Sheridan | 128/347 |
| 3,688,773 | 9/1972 | Weiss | 128/305 |
| 3,817,250 | 6/1974 | Weiss et al. | 128/305 |
| 3,886,946 | 6/1975 | Hyde | 128/305 |
| 4,331,138 | 5/1982 | Jessen | 128/200.26 |
| 4,440,161 | 4/1984 | Wadhwa | 128/207.29 |
| 4,465,068 | 8/1984 | Cantu | 128/207.29 |
| 4,520,810 | 6/1985 | Weiss | 128/200.26 |
| 4,677,978 | 7/1987 | Melker | 128/207.29 |
| 5,217,005 | 6/1993 | Weinstein | 128/200.26 |
| 5,217,007 | 6/1993 | Ciaglia | 128/207.29 |

*Primary Examiner*—Aaron J. Lewis
*Attorney, Agent, or Firm*—Garvey, Smith, Nehrbass & Doody

[57] ABSTRACT

An apparatus for performing emergency tracheostomies, by inserting the apparatus into the trachea of a patient, the apparatus including an air delivery tube, having a body portion, a first upper threaded end, a second lower end, and a bore extending throughout the body portion to accommodate air flow through the air delivery tube; a trocar member including a body portion insertable through the bore of the air delivery tube, with a pointed end partially protruding out of the second lower end of the tube for piercing the tracheal wall during insertion of a portion of the air delivery tube into the trachea; an extendor portion engageable to the first upper end of the air delivery tube after the tube has been inserted into the trachea, and the trocar member has been removed from the air delivery tube, for providing a point of delivering air flow through the air delivery tube into the trachea of a patient above the tracheal wall; the air delivery tube and trocar insertable in the extendor member and sealed therein when not in use.

13 Claims, 3 Drawing Sheets

EMERGENCY TRACHEOSTOMY APPARATUS

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to emergency medical procedures. More particularly, the present invention relates to an apparatus which can be assembled to provide a device for performing an emergency tracheostomy on a patient and establishing an oxygen path to the lungs manually or securable to a pump apparatus.

2. General Background

Quite often, emergency medical procedures must be performed on individuals in public, when no sophisticated equipment is available. One of the most common medical emergencies is when a person inadvertently lodges a mass of food, such as meat, or other foreign object in his windpipe, and is rendered unable to breathe, or suffers a reaction and internal swelling of the windpipe impedes or interrupts airflow to the lungs. The Heimlich maneuver has become a very popular method of dislodging foreign objects from a person's windpipe. However, quite often the foreign object of mass of food is so firmly lodged that the Heimlich maneuver will not succeed. Likewise, when a person suffers a reaction, and internal swelling occurs, the Heimlich maneuver, of course, is of no avail. Therefore other emergency procedures must be undertaken to restore the person's breathing and save his life.

Additionally, the emergency medical procedure is required when a patient suffers from a heart attack or other emergency which interrupts the breathing of the patient, and the patient goes into cardiopulmonary arrest. It is necessary, therefore, when this occurs, that again emergency procedures be undertaken to restore the person's breathing while waiting for the insertion of an endotracheal tube which would provide a permanent source of oxygen into the lungs.

A very common procedure which is done on an emergency basis in order to supply air to a persons lungs on an emergency basis is a tracheostomy. A tracheostomy is a procedure which should be performed by trained medical personnel. If a person involved in such a medical situation is fortunate, there may be a doctor or the like person available to perform the procedure. What is involved is the making of a small incision in the windpipe directly below the larynx, so as to expose the windpipe, so that air may flow into the person's lungs, through the incision, until the foreign object is dislodged, or the windpipe is restored to its normal functioning. In most cases, it is preferable that a tube be inserted in the incision, and down the windpipe to assure that the air flow is unimpeded until further medical procedures can be undertaken.

The difficulty in undertaking this procedure as described is multi-fold. First, the windpipe wall must be sliced by a razor or scalpel in order to expose the pipe to air flow or the introduction of a tube, causing a severe loss of blood. Secondly, following the incision with a scalpel or other blade, a plastic tube should be inserted into the incision and down the windpipe, perhaps causing more trauma to the patient. Thirdly, the person suffering the emergency must be fortunate enough to have a medical person available who possesses a scalpel or sharp, hopefully sterile blade on his person, and likewise, possesses a tube to insert into the incision. Such a combination, in all likelihood would be rare, and the person would have to be exposed to yet more trauma and unsanitary conditions.

SUMMARY OF THE PRESENT INVENTION

The apparatus of the present invention solves the problems in the art in a simple and straightforward manner. What is provided is an apparatus for performing emergency tracheostomics, by inserting the apparatus into the trachea of a patient, the apparatus including an air delivery tube, having a body portion, a first upper threaded end, a second lower end, and a bore extending throughout the body portion to accommodate air flow through the air delivery tube; a trocar member including a body portion insertable through the bore of the air delivery tube, with a pointed end partially protruding out of the second lower end of the tube for piercing the tracheal wall during insertion of a portion of the air delivery tube into the trachea; an extendor portion engageable to the first upper end of the air conveying tube after the tube has been inserted into the trachea, and the trocar member has been removed from the air delivery tube, for providing a point of delivering air flow through the air delivery tube into the trachea of a patient above the tracheal wall; the air delivery tube and trocar insertable in the extender member and scaled therein when not in use.

Therefore, it is a principal object of the present invention to provide an apparatus for performing emergency tracheostomies in the event that a person goes into cardiopulmonary arrest;

It is a further object of the present invention to provide an apparatus for performing emergency tracheostomies which eliminates the need for a scalpel, and the need for introducing a tube into the windpipe following an incision by the scalpel;

It is a further object of the present invention to provide an apparatus for performing emergency tracheostomics which utilizes a single needle puncture into the skin and windpipe of the person, thus eliminating the use of a scalpel and incision;

It is a further object of the present invention to provide an apparatus for performing emergency tracheostomies which is extendable outward and away from the person's throat so that a doctor or the like may blow into the apparatus manually, or may attach an air pump line thereto for providing a flow of air to the person;

It is a further object of the present invention to provide an emergency tracheostomy apparatus which utilizes a single barrel of a needle in order to make the opening in the windpipe wall while providing a bore for allowing airflow into the windpipe;

It is a further object of the present invention to provide an emergency tracheostomy apparatus which, following its insertion into the windpipe of a person, does not have to be removed from the windpipe in order to allow an endotracheal tube to be inserted through the windpipe on a more permanent basis;

It is a further object of the present invention to provide an emergency tracheostomy apparatus which can be carried in one's pocket, easily assembled for use, and easily restored for non-use by the user.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
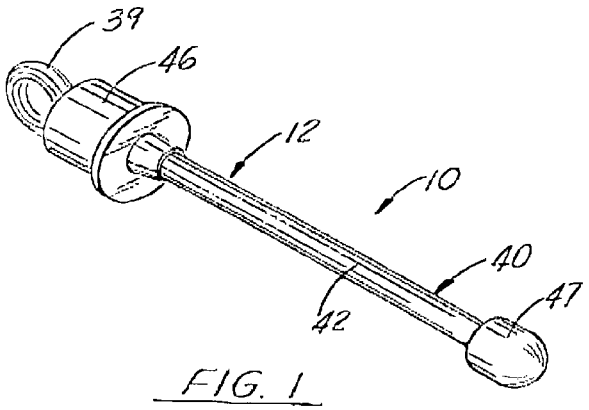
FIG. 1 illustrates an overall perspective view of the preferred embodiment of the apparatus of the present invention.
Figure 3:
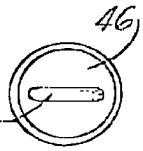
FIG. 3 illustrates a top view of the preferred embodiment of the apparatus of the present invention.

FIGS. 1 through 8 illustrate the preferred embodiment of the assembly comprising the apparatus of the present invention by the numeral 10. In general, the principal components comprising the assembly 10 would include a principal air delivery tube 12, a trocar member 28 and an extendor 40. Turning now to the structure and functioning of these individual components, and as illustrated in the figures, the principal air delivery tube 12 would generally comprise an elongated shaft portion 14, having an annular sidewall 16, a flat edge 18 on the first lower end 20, and an enlarged housing 22 on the second upper end 24 of air delivery tube 12. The enlarged housing 22 would further include a threaded inner wall (phantom lines 23), the function of which will be discussed further. There is further provided a continuous bore 26 through the entire air delivery tube 12, for transmitting fluids and gas or air therethrough during use.

As seen in the figures, there is provided a trocar member 28, having a solid elongated rod portion 30, which is slightly longer than the shaft portion 14 of air delivery tube 12. Rod portion 30 would be of a continuous diameter slightly smaller than the inner diameter of the bore 26 through air delivery tube 12, so that the rod portion 30 would slide into the bore 26 of air delivery tube 12, with the end 32 of rod portion 30 protruding from the end 20 of air delivery tube 12. End 32 of rod 30 would comprise a plurality of bevelled sides 34, defining point 38, so as to define a means for easily inserting the lower end 32 of rod 30 into the trachea of a patient without having to properly align the end 32 of rod 30 in a particular angular alignment. The second end 35 of trocar member 28 comprises an enlarged portion 36, having an outer threaded wall 37, and a top portion 39. The top 39 includes a bore 41 therethrough for threading a key chain 45 (FIG. 2) or the like in order to transport the assembly 10.

In order to complete the assembly, there would be further included a third portion to the assembly 10, which comprises an extender 40, which includes an elongated housing 42, having a lower threaded first end 44, an enlarged upper end 46, likewise defining an annular wall 48, defining a hollow interior 50. Hollow interior 50 continues through elongated portion 42 to define a continuous bore 41 through extender 40. The interior of wall 48 would be threaded via threads (phantom line 49) to accommodate the top 36 of trocar 28 which will be fully defined further. Dimensionally, the interior bore of extender 40 would be of sufficient diameter to accommodate the shaft portion 14 of air delivery tube 12 housing trocar member 28 therein as will be discussed further.

Figure 2:
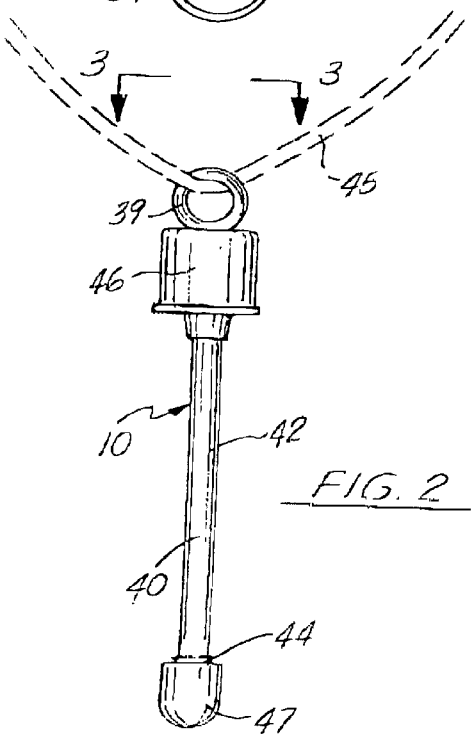
FIG. 2 illustrates a side view of the preferred embodiment of the apparatus of the present invention.
Figure 4:
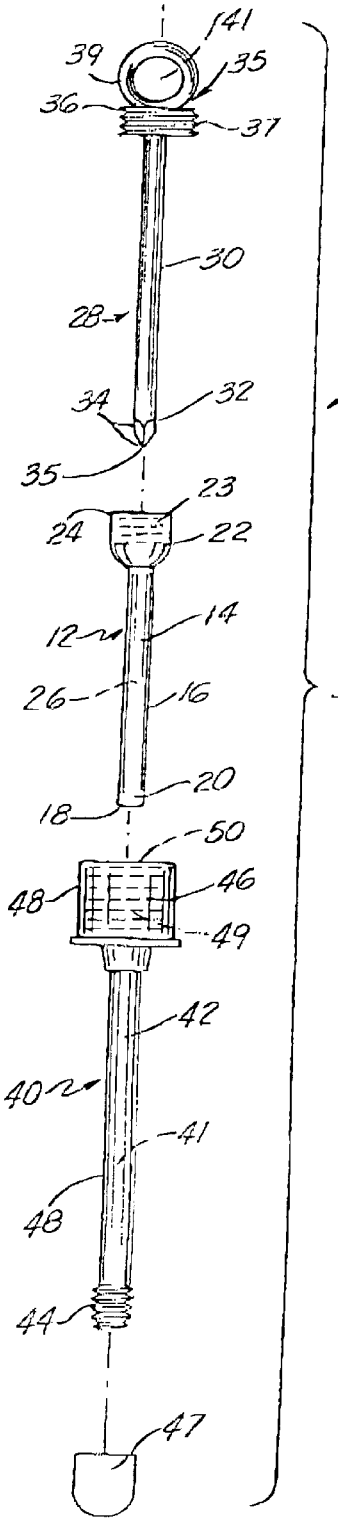
FIG. 4 illustrates an overall exploded view of the components of the preferred embodiment of the apparatus of the present invention.

Turning now to the method of assembling the components of assembly 10, reference is made to FIGS. 1 through 4. As seen in exploded view in FIG. 4, when assembly 10 is not in use, the shaft 14 of principal air delivery tube 12 is slidably accommodated within the bore 52 of housing 42, and the enlarged housing 22 of air delivery tube 12 is positioned within the enlarged upper end 42 of extender 40. The trocar member 28 would then be slidably positioned within the bore 26 of principal air delivery tube 12. At this point the upper threaded portion 36 of trocar member 28 is threaded to the interior surface 49 of housing 42, so as to define a sealed upper connection of the assembly 10, with the top 39 of trocar member 28 defining a means to engage the key chain 45 through bore 41 in order to carry the assembly 10. The lower end 44 of housing 42 is then sealably close via a cap member 47 threaded to the lower end 44 of housing 42, in order to complete the sealing of the trocar 28 and air delivery tube 12 within extender 40 while not in use, as seen in FIGS. 1 and 2.

Figure 5:
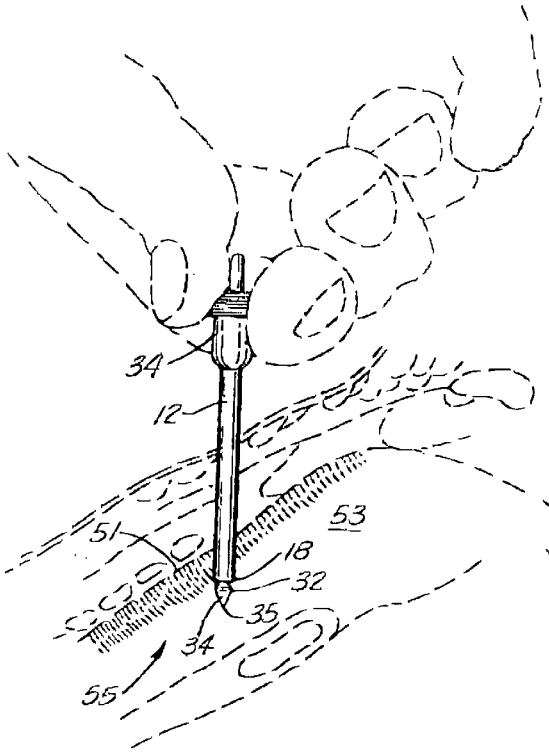
FIGS. 5 and 6 illustrate the insertion of the apparatus of the present invention into a trachea of a patient.

Turning now to the functioning of assembly 10, reference is made to FIGS. 5 through 8. When a person is in need of a tracheostomy, as discussed earlier, the doctor or other medical person having the assembly 10 would threadably disengage the upper end 34 of trocar member 28 from extender 40 and the lower cap 47 from the lower end 44 of extender 40. The trocar member 28 and the principal air delivery tube 12 would be removed from the extender 40, while the trocar member 28 is still housed within air delivery tube 12. The air delivery tube 12, together with the trocar 28 extending through air delivery tube 12 would then be inserted into the wall 51 of the trachea 55 of the person in need, at an angle so as to provide that the angle of the position of the end 18 of air delivery tube 12 would be down toward the lungs, and projecting away from the voice box. Again, it should be emphasized that because the end 32 of trocar member 28 includes a plurality of beveled sides 34, to define point 35, the trocar 28 can be inserted quite easily (as seen in FIG. 5), without having to undertake any alignment of the end, as one would have to do should there only be a single beveled edge. During the time that the rod 30 is being fully inserted through the tracheal wall 51, the trocar member 28 would serve to disallow any flesh from clogging the bore 26 of the principal air delivery tribe 12, until the air delivery tube 12 is fully inserted through the tracheal wall 51, and extends into the air flow passage 53 through the trachea. As seen in the FIGURES, once the air delivery tube 12 has been fully inserted into the wall 51 of the trachea 55, there is still sufficient space within the windpipe to introduce an endotracheal tube through the patient's mouth into the windpipe and down into the lungs, without the air delivery tube 12 blocking the introduction of that more permanent source of oxygen.

Figure 6:
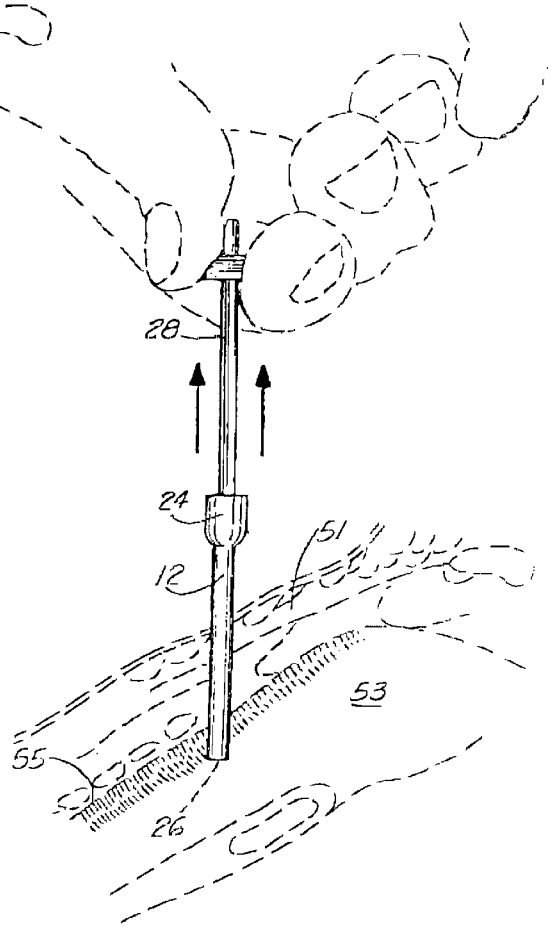
Figure 7:
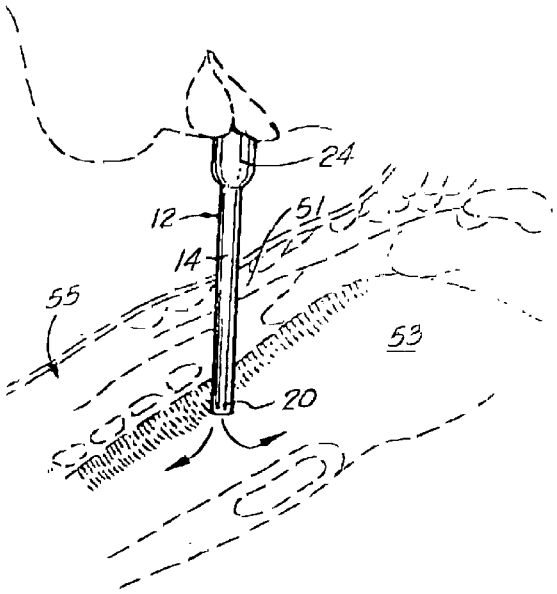
FIG. 7 illustrates air being administered manually into the trachea of a patient through the apparatus of the present invention.
Figure 8:
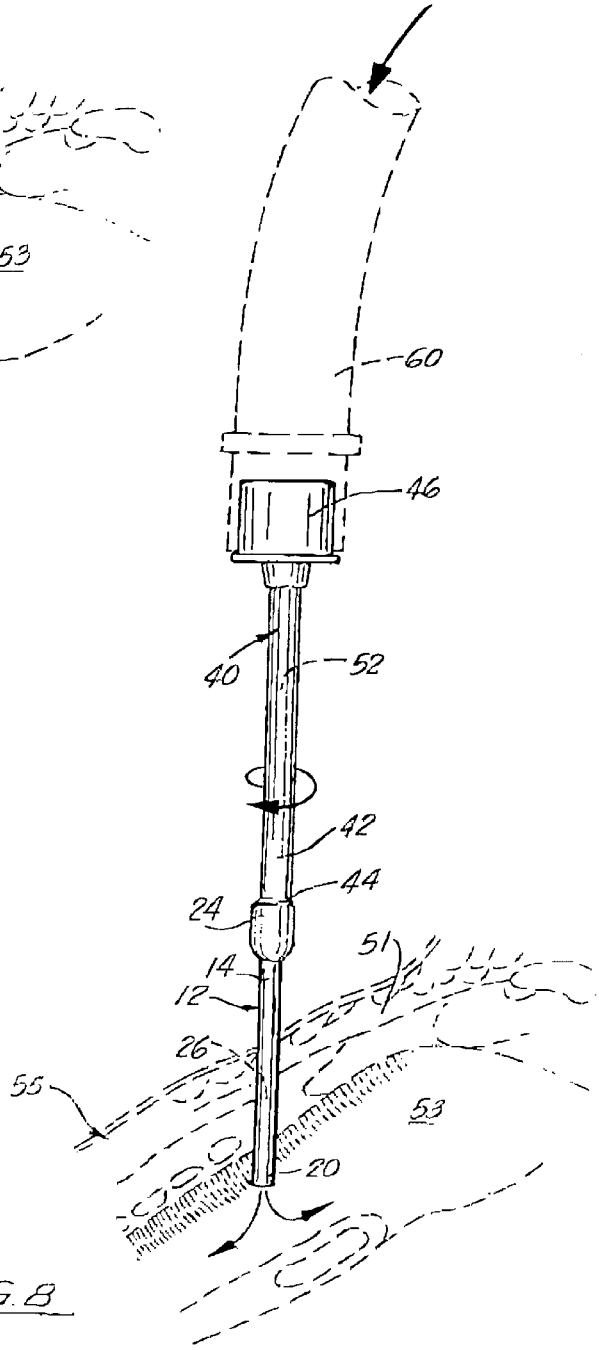
FIG. 8 illustrates air being administered via an air line into the trachea of the patient through the apparatus of the present invention.

In FIG. 6, the trocar 28 would then be removed from the air delivery tube 12, so as to allow air to begin flowing to the patient's lungs, through the bore 26 within air delivery tube 12. The only remaining portion of air delivery tube 12 outside of the patient's body is the upper portion 24, which would lie very close to the patient's outer skin. At this point, turning to FIG. 7, the lower threaded end 44 of extender 40 would then be threadably engaged to the upper threaded end 23 of air delivery tube 12 to define an assembled unit for use on the patient. The position of the housing 22 secured to the air delivery tube 12 provides for easier access to assembly 10 in order to introduce forced air flow through the assembly and into the patient in order to keep the patient with air supplied to his lungs, as seen in FIG. 8.

The means for introducing air flow may be an air flow line 60 secured to the upper end 46 of extender 40, which would receive air from a manually operated or power air pump means so that a constant flow of air is provided. In the more extreme emergencies a person, as seen in FIG. 7, such as a doctor or medic, would simply blow into the upper end 24 of the air delivery tube 12, or following the threading of the housing 42 thereto, manually blow air through the end 46 of housing 42 and air delivery tube 12, until another more permanent source of fresh air would be available.

As was stated earlier, when not in use, the assembly would be assembled as recited earlier, and could easily be transported in ones pocket, briefcase, or at the end of a key chain. The compact nature of the assembly provides for quick and easy access for emergency use, and further provides for easy insertion and delivery of air to the patient in need.

The following table lists the part numbers and part descriptions as used herein and in the drawings attached hereto.

PARTS LIST

| Description | Part No. |
|---|---|
| assembly | /10 |
| air delivery tube | 12 |
| shaft portion | 14 |
| annular sidewall | 16 |
| flat edge | 18 |
| first lower end | 20 |
| enlarged housing | 22 |
| phantom lines | 23 |
| second upper end | 24 |
| bore | 26 |
| trocar member | 28 |
| rod portion | 30 |
| lower end | 32 |
| bevelled side | 34 |
| second side | 35 |
| enlarged portion | 36 |
| outer threaded wall | 37 |
| point | 38 |
| top portion | 39 |
| extendor | 40 |
| bore | 41 |
| elongated housing | 42 |
| first lower end | 44 |
| key chain | 45 |
| enlarged upper end | 46 |
| cap member | 47 |
| annular wall | 48 |
| phantom lines | 49 |
| interior | 50 |
| wall | 51 |
| air flow passage | 53 |
| trachea | 55 |
| air flow line | 60 |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An apparatus for performing emergency tracheostomies, comprising:

a) an air delivery tube, having a body portion, a first end, a second end, and a bore extending throughout the body portion to accommodate air flow through the air delivery tube;

b) a trocar member including a body portion insertable through the bore of the air delivery tube, with a pointed end partially protruding out of the second lower end of the air delivery tube;

c) extendor means engageable to a first upper end of the air delivery tube defining a means to provide air flow through the air delivery tube into a trachea of a patient; and d) a lower cap portion engageable on a lower end of the [body portion of the trocar member] *extendor means* so that the air delivery tube is maintained in the trocar member during non use.

2. The apparatus in claim 1, further comprising a threaded portion on an upper end of the air delivery tube for threadably engaging the extendor means thereto for air delivery.

3. The apparatus in claim 1, wherein the trocar member is removable from the air delivery tube before the extendor means is threadably engaged to the air delivery tube.

4. The apparatus in claim 1, wherein the extendor means further comprises a bore through a body portion of sufficient length and diameter so as to accommodate the air delivery tube within the bore of the extendor means when the air delivery tube is not in use.

5. The apparatus in claim 1, wherein the trocar member is positioned within the air delivery tube when the air flow tube is housed within the extendor means, and a top portion of the trocar member is threadably engaged to a top portion of the extender means during non-use.

6. The apparatus in claim 1, further comprising a loop on the top of the extendor means for threading a key chain therethrough for carrying the apparatus during non-use.

7. The apparatus in claim 1, wherein the air delivery tube is sufficiently small to allow the insertion of an endotracheal tube down the patient's windpipe without having to remove the air delivery tube from the windpipe.

8. The apparatus in claim 7, further comprising a threaded portion on an upper end of the air delivery tube for threadably engaging the extendor portion thereto for air delivery after the trocar member has been removed from the air delivery tube.

9. The apparatus in claim 7, wherein the extendor means further comprises a bore through a body portion of sufficient length and diameter so as to accommodate the air delivery tube within the bore of the extendor means when the air delivery tube is not in use.

10. The apparatus in claim 7, wherein the trocar member is positioned within the air delivery tube when the air delivery tube is housed within the extendor portion, and a top portion of the trocar member is threadably engaged to a top portion of the extendor portion during non-use.

11. The apparatus in claim 7, further comprising a loop on the top of the extendor portion for threading a key chain therethrough for carrying the apparatus during non-use.

12. An apparatus for performing emergency tracheostomies, by inserting the apparatus into the trachea of a patient, the apparatus comprising:

a) an air delivery tube, having a body portion, a first end, a second end, and a bore extending throughout the body portion to accommodate air flow through the air delivery tube;

b) a trocar member including a body portion insertable through the bore of the air delivery tube, with a pointed end partially protruding out of the second lower end of the tube for defining a means to pierce the tracheal wall during insertion of a portion of the air delivery tube into the trachea;

c) an extendor portion engageable to a first upper end of the air delivery tube after the tube has been inserted into a trachea, and the trocar member has been removed from the air delivery tube, for providing a point of delivering air flow through the air delivery tube into a patient's trachea above the tracheal wall; and d) a lower cap portion engageable on a lower end of the [body portion of the trocar member] *extendor portion* so that the air [deliver] *delivery* tube is sealed in the trocar member during non-use.

13. An apparatus for performing emergency tracheostomies, which may be carried by a person in a disassembled configuration, and may be used to perform tracheostomies in an assembled configuration, the apparatus in the disassembled configuration comprising:

a) an air delivery tube, having a body portion, a first end, a second end, and a bore extending throughout the body portion to accommodate air flow through the air delivery tube;

b) a trocar member including a body portion insertable through the bore of the air delivery tube, with a first pointed end partially protruding out of the second lower end of the tube for defining a means to pierce a patient's tracheal wall during insertion of a portion of the air delivery tube into a patient's trachea and a second upper end having an outer threaded wall protruding from the first end of the air delivery tube;

c) an extendor portion having an elongated body portion, with a diameter sufficient to accommodate the air delivery tube housing the trocar therein, and an upper body portion of sufficient diameter to threadably engage the upper threaded wall of the trocar member; and d) a cap *for* threadably [for] engaging to the lower end of the extendor portion for sealing the lower end of the extendor portion.

* * * * *